United States Patent [19]

Henderson

[11] Patent Number: 5,537,045
[45] Date of Patent: Jul. 16, 1996

[54] DETECTION AND LOCATION SYSTEM FOR MONITORING CHANGES IN RESISTIVITY IN THREE DIMENSIONS

[76] Inventor: Michael E. Henderson, 3068 Bramble Dr., Reno, Nev. 89509

[21] Appl. No.: 324,415

[22] Filed: Oct. 17, 1994

[51] Int. Cl.[6] .......................... G01N 27/20; G01R 27/14
[52] U.S. Cl. .................. 324/557; 324/522; 324/715; 324/718; 324/722
[58] Field of Search ............................ 324/522, 557, 324/713, 715, 718, 722

[56] References Cited

U.S. PATENT DOCUMENTS

| | | | |
|---|---|---|---|
| 3,319,158 | 5/1967 | McDoullett et al. | 324/9 |
| 3,383,863 | 5/1968 | Berry | 61/1 |
| 4,166,244 | 8/1979 | Woods et al. | 324/65 R |
| 4,296,379 | 10/1981 | Yoshizumi | 324/357 |
| 4,404,516 | 9/1983 | Johnson, Jr. | 324/54 |
| 4,467,283 | 8/1984 | Owen et al. | 324/363 |
| 4,644,354 | 2/1987 | Kidd | 340/870.27 |
| 4,905,210 | 2/1990 | Owen | 367/128 |
| 4,947,470 | 8/1990 | Darilek | 324/557 |
| 4,959,639 | 9/1990 | Benson | 340/618 |
| 5,008,627 | 4/1991 | Tsutsuta et al. | 324/715 X |
| 5,357,202 | 10/1994 | Henderson | 324/557 |

*Primary Examiner*—Kenneth A. Weider
*Assistant Examiner*—Glenn W. Brown
*Attorney, Agent, or Firm*—Bernhard Kreten

[57] ABSTRACT

A method and apparatus is provided for monitoring and locating the presence of fluids leaking from a containment vessel. A multiplicity of probes having conductive affinity are strategically oriented adjacent the containment vessel and periodic surveillance is made relying on conductivity of the sub-surface media within which the probes have been placed, such that disturbances in the conductivity correlate with migration of the leaking fluid. The method and apparatus may be utilized to detect migration of salinated fluids into a region where previously less salination existed. The probes can be oriented adjacent a surface and yet determine a conductivity of the sub-surface media at a plurality of different pseudo-points having varying depths. The presence, location and extent of a leak can thus be monitored.

35 Claims, 5 Drawing Sheets

DETECTION AND LOCATION SYSTEM FOR MONITORING CHANGES IN RESISTIVITY IN THREE DIMENSIONS

FIELD OF THE INVENTION

This invention relates generally to detecting and locating leaks in liquid containment systems. More specifically, this invention relates to detecting soil moisture, indicative of conductive solution leaks from an impoundment, by monitoring a conductivity of subsurface media surrounding the impoundment or region in which soil moisture and soil conductivity information is needed.

BACKGROUND OF THE INVENTION

Containing materials in a specified area is a concern in many industrial enterprises. One of the more conspicuous manifestations of containment includes the sequestration of hazardous waste materials. Should such materials escape from the containment facility in which they are impounded, substantial harm could result, both ecologically and economically. To remedy this potential problem, more responsive techniques for detecting leakage from such facilities are needed.

Difficulties that have arisen with regard to leak detection include, inter alia, variations in one or more qualitative characteristics of the material sought to be contained. This makes characteristic specific sensor calibration critical. Another problem is the containment facility can leak from any containment surface or edge and the composition of the container may have to vary because of the material to be combined. Moreover, conditions in the ground surrounding the facility may not necessarily be constant. Thus, monitoring the facility for leakage can be a very resource intensive error. Various schemes have been offered for remedying one or some of these difficulties in the past. However, the problems persist, and a better leakage detection system is still a highly sought after commodity.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| INVENTOR | PATENT NO. | ISSUE DATE |
| --- | --- | --- |
| McDoullett, et al. | 3,319,158 | May 9, 1967 |
| Berry, J. B. | 3,383,863 | May 21, 1968 |
| Woods, et al. | 4,166,244 | August 28, 1979 |
| Yoshizumi | 4,296,379 | October 20, 1981 |
| Johnson, Jr. | 4,404,516 | September 13, 1983 |
| Owen, et al. | 4,467,283 | August 21, 1984 |
| Kidd | 4,644,354 | February 17, 1987 |
| Owen | 4,905,210 | February 27, 1990 |
| Darilek | 4,947,470 | August 7, 1990 |
| Benson | 4,959,639 | September 25, 1990 |

The patent to Berry teaches the use of a leak detector especially for ponds, tanks or pit liners where the leak is located by a change in electrical resistance around two sets of wires disposed underneath the liner and separated by some previous insulating media. In one form of the invention, liquid from a cavity seeps through a normally impervious coat or liner through a leak such that it will dampen the previous insulating material thus altering the electrical resistance between wires. One limitation of this resistance measuring method is that it has difficulty discerning other present subjacent liquids from those contained in the impoundment. Another limitation is that once a leak does occur, such material may persist in the previous insulating media such that future leaks may not be detected. Another limitation is that only point sources are utilized rather then field sources, limiting this device to leak detection without determining the leak's location. A further limitation is that the relatively fragile bare wires used are subject to potential corrosive and deleterious exposure to material such that these essential wires may be permanently destroyed.

Alternatively, the patent to Woods, et al. teaches the use of an electric field produced by application of current to a metallic reference ring surrounding a tank and a metallic portion of that tank. Leaks from the tank are detected by potential changes in the field as are measured between electrodes placed within the field and the tank. A limitation of this potential variation device is that it is slow, if not incapable in some cases, to detect a leak from the bottom of a tank as opposed to the sides of a tank. A further limitation is that in the form presented, physical attachment to a metallic portion of the tank is required. For applications that do not include a metallic tank, a problem arises.

Likewise, the patent to Johnson teaches the use of a network of electrically conductive wires placed under a reservoir wherein the wires are constructed so that point source only not field source chemicals escaping through a leak will corrode the wires or alternatively degrade the insulation around the wires thereby causing a change in the electrical properties of the wire. One limitation of this system is that should a leak occur, future leak detection may be impossible, due to the necessity of corroding the means of discovering the leak. Another limitation of this system is that it requires actual physical contact of the leaking material and the detecting medium. If the leak is shallow, or if the leak happens to pass between the wires, as opposed to over the wires, the leak will not be detected. A further limitation is that only a point source is utilized as opposed to a field source.

The patent to Kidd teaches the use of an apparatus for detecting the presence of fluid comprised of a sensing means buried on either side of a tank. In particular, the apparatus will indicate whether the condition next to the tank is dry, or whether a polar or non-polar liquid is present. An important limitation of this apparatus is its failure to detect a leak that might occur at the bottom of the tank and continue in a downward direction without ever being detected by the sensing devices next to the tank. Another limitation of the apparatus is that its application has been tailored to predominantly support the peculiarities of a service station environment.

Another patent, issued to Owen, teaches the use of a boat and radio transmitter combination to locate a leak in a liquid impoundment. By use of the radio transmitter the location of the boat can be determined when it detects a leak. A clear limitation of this system would involve the use of a corrosive liquid in the impoundment. Such a liquid would corrode the boat and eventually require its replacement. A further limitation of this system is that radio waves are subject to a myriad of interference problems. Should interference occur, it could lead to leaks either not being detected or being misdetected. Yet another limitation of the system is that when a leak is detected, the migration of the leak cannot be monitored, making remedial efforts far more difficult.

The patent to Darilek teaches the use of an array of electric or magnetic field detectors which are placed on one side of the liner of an impoundment. A voltage is impressed across the liner and the impounded material such that when a leak occurs, a current flows through the leak, creating an electrical field and a magnetic field around the leak whose source can be located geometrically. One limitation of this apparatus is the requirement of locating a voltage impressing electrode in the material impounded. It should be noted that if the impounded material were highly corrosive, the electrode would degrade and need eventual replacement. A further limitation is that if a leak is detected, that leak's further migration cannot be monitored by this apparatus, making remedial measures more difficult.

The Benson patent teaches the use of a flexible rod and sleeve assembly to detect the presence of leaking petroleum. The apparatus detects leaking petroleum on its way toward the water table by being constructed of a material which when contacted by petroleum (but not water) will erode and cause the sleeve to move upward activating an alarm. A clear limitation of this assembly is that the material it is intended or able to detect leaks for is petroleum (or other hydrocarbon materials). This very narrowly tailored invention is designed to detect but one very specific type of leak.

The patent to Yoshizumi teaches a system for ground prospecting which includes injecting liquid chemical into the ground and monitoring resistance change in the ground which results. The present invention of this application is distinguishable from Yoshizumi in that, inter alia, a method and system are provided for detecting where and when a leak of liquid has occurred.

The remainder of the prior art listed above but not specifically distinguished diverge even more starkly from the present invention than those specifically distinguished above.

SUMMARY OF THE INVENTION

Minerals, rocks, and soil, in different measure, can conduct electricity. The capability of soil or rock material to be effective or ineffective conductors is influenced by characteristics such as particle composition, density, the degree of pore space saturation and the chemical composition of any interstitial fluid (fluid in the spaces between the particles).

A leak from a waste or liquid impoundment facility consists of either conductive or non-conductive fluid which changes the electrical resistivity of material with which it contacts. Liquid leaking through a geomembrane (e.g. plastic liner) will soak the subgrade beneath. Electricity will then pass through these soils with a greater or lesser ease than before the leak occurred. Regularly measuring the difference in resistivity—or its inverse, conductivity—will allow comparisons of the current data with the average to date. Large differences occur and continue to change in magnitude as a leak progresses. By monitoring the locality of such resistivity changes, any leakage from a system will not merely be detected, but also pin-pointed to a particular spatial location.

Unfortunately, resistivity (or conductivity) cannot be measured directly. However, it can be computed if other quantities are measured. These quantities may include the intensity of a current injected into the medium and the magnitude of a potential/voltage established between measurement electrodes resulting from the current. The value of voltage measured depends on the geometry of the electric field, the nature of the soils and interstitial fluids, and the method selected to measure the quantities.

The present invention contemplates converting the measured potential to a conductivity value, then stores that value along with the spatial coordinates of the sampling station in a unique file. A computer program then compares the calculated values with the previous statistical average for each station and creates a file that represents the calculated offset (difference) of the current data from the previous average. The program then calculates a new average and stores the values and adds the information to an archive to preserve each individual measured value. The result is an ASCII file (in standardized computer code) that contains values for the position and conductivity of each measuring station in the electrode grid and another file with the offset of the current values from a statistical mean.

Thus, an apparatus is provided by which a leak from a storage facility may be first quickly detected and second pin-pointed in three dimensions by means of monitoring the conductivity of the subjacent soil. The apparatus includes an array of electrodes preferably arranged to be harnessed in groups of four. The electrodes produce a field by which its potential and current, and thus resistivity may be measured. When a leak occurs, the conductivity of the soil increases or decreases depending on the conductivity of the fluid leaking so that the apparatus will detect and locate that leak.

An alternative use of this apparatus is in detecting soil moisture characteristics of surface media or the migration of salinated water into existing previously-fresh-water aquifers, or other solutions with distinctly different resistivity from the background such as with unsaturated flow monitoring associated with contaminant plumes. The electrodes sense reduced resistivity due to the lower resistance of salt water compared to fresh water.

OBJECTS OF THE INVENTION

A primary object of the present invention is to provide a novel and useful leak detector and locator.

A further object of the present invention is to provide a device as characterized above which detects leaks emanating from a tank, pipe or any other storage or impoundment facility.

A further object of the present invention is to provide a device as characterized above which locates and monitors the migration of leaks from an impoundment facility in three dimensions.

A further object of the present invention is to provide a device as characterized above which detects relatively small leaks in a relatively small area.

A further object of the present invention is to provide a device as characterized above which detects leaks by means of a system completely external to the impoundment facility.

A further object of the present invention is to provide a device as characterized above which detects leaks regardless of prevailing or changing soil conditions.

A further object of the present invention is to provide a device as characterized above which detects leakage of both conductive and non-conductive materials.

A further object of the present invention is to provide a device as characterized above which determines the salinity of an aquifer in a region surrounding a water well.

A further object of the present invention is to provide a device as characterized above which can determine whether or not an impoundment such as a tank is leaking, how much liquid is leaking from the tank, and what the horizontal and vertical extent is of a plume of the leaking liquid.

Another further object of the present invention is to provide a method for determining a conductivity at a plurality of pseudo-points within a region of sub-surface media, the conductivity indicative of soil moisture at these pseudo points and the occurrence of an event such as a leak from an impoundment.

Another object of the present invention is to provide a system for monitoring conductivity of sub-surface media which can be calibrated to account for particular characteristics of the sub-surface media to be monitored.

Another object of the present invention is to provide a system which can detect a conductivity of sub-surface media at various different depths through probes adjacent a surface overlying the sub-surface media.

Another object of the present invention is to provide a method for detecting soil moisture changes in an agricultural region to improve crop performance.

Another object of the present invention is to provide a system which can detect the extent of contamination of soil in an agricultural region.

Another object of the present invention is to provide a system which can detect sub-surface movement of soil particles by detecting changes in soil conductivity resulting from changes in soil compaction.

Viewed from a first vantage point, it is an object of the present invention to provide an apparatus for detecting and locating a leak from an impoundment, the impoundment confining a substance to be impounded above a soil substrate, the apparatus comprising, in combination: the soil substrate underlying and conformed to mirror the impoundment; a plurality of sensing means detecting variations in potential difference between each individual sensing means and other proximate sensing means; a current supply directed to a region proximate to the sensing means such that an electric field is established between the sensing means when the current supply is energized; each of the sensing means oriented in a fixed location embedded within the soil substrate; the sensing means including a coating allowing the sensing means to maintain an electrical connection with the surrounding soil yet avoid degradation caused by contact with the soil and other corrosive compounds underlying the impoundment; the impoundment provided with a substance, which when admitted to the soil substrate alters the potential difference between the sensing means; and monitoring means operatively coupled to the plurality of sensing means for detecting any change in the potential difference.

Viewed from a second vantage point, it is an object of the present invention to provide a system for monitoring the soil beneath an impoundment of fluid to be confined for the presence of a leak in the impoundment, comprising, in combination: a plurality of electrodes, each having directional sensitivity and all mutually oriented with respect to one another such that when a current is impressed on any one pair of electrodes by a source of current, a potential profile is impressed upon another pair, the electrodes permanently embedded beneath the impoundment such that a leak from the impoundment changes the potential profile between the electrodes, and monitoring means coupled to the electrodes to monitor and calculate values of the potential.

Viewed from a third vantage point, it is an object of the present invention to provide a system for monitoring changes in the salinity of portions of an underground aquifer comprising in combination: a plurality of electrodes oriented in an array and having directional sensitivity such that when an electric current from a current source is impressed on two electrodes of the array a potential difference is imposed between two other electrodes in the array, the electrodes positioned along a region where salinated water migration is suspected; wherein a computation means is operatively coupled to the electrodes and calculates the potential difference between the electrodes, the computation means including a means to determine a resultant resistivity of underground soil between the electrodes; wherein the computation means includes a means for calculating a difference between more recent resistivity and previous resistivity at each electrode; and wherein a switching means is interposed between the current source and the electrodes, the switching means also interposed between the computation means and the electrodes, such that the electrodes can be connected and disconnected iteratively to either the current source or the computation means; whereby when salinated water penetrates soil surrounding the electrodes, the resistivity of the soil is decreased due to the different electrolytic properties of salinated water indicating that salinated water migration is occurring.

Viewed from a fourth vantage point, it is an object of the present invention to provide a method for detecting changes in conductivity of sub-surface media, indicative of an event such as a leak, including the steps of: orienting a plurality of probes in a grid with each probe having at least a portion thereof beneath a surface overlying a sub-surface region to be monitored, each probe formed to include conductive material exposed on a surface of the probe, the conductive material in contact with media beneath the surface; coupling each probe electrically to a switching means, the switching means including means to selectively connect two of the probes to a volt meter; impressing a current into the sub-surface media; operating the switching means to couple a first set of two probes to the volt meter such that the two probes become voltage monitoring probes; measuring a voltage between the two probes; calculating a conductivity of sub-surface media between the first set of probes by dividing the current by the voltage; re-operating the switching means to couple a second set of two probes to the volt meter; determining a conductivity of sub-surface media between the second set of probes by repeating the measuring step and the calculating step for the second set of probes; continuing to re-operate the switching means and repeat the determining step until the region identified for event monitoring has been covered.

Viewed from a fifth vantage point, it is an object of the present invention to provide a system for monitoring conductivity of subsurface media, comprising in combination: a plurality of probes, each probe including an electrically conductive material exposed on a surface of the probe and means to couple the probe electrically to other components of the system, the probes including means to allow burial thereof at least partially beneath a surface overlying a region of sub-surface media to be monitored, a power source having two output nodes and means to impose a voltage between the output nodes, a volt meter having two sensing nodes, means to measure a voltage between said sensing nodes, and means to communicate a voltage measured by the measuring means to an output device, and a switching means including: means to selectively electrically couple each of the two output nodes to a different one of a first pair of the probes, such that said first pair of the probes become active probes delivering current into a portion of the sub-surface media between the active probes, means to selectively electrically couple each of the two sensing nodes to a different one of a second pair of the probes, such that the second pair of the probes become monitoring probes monitoring a voltage between the monitoring probes caused by the current between the active probes.

These and other objects will be made manifest when considering the following detailed specification when taken in conjunction with the appended drawing figures.

DESCRIPTION OF PREFERRED EMBODIMENTS

Figure 1:
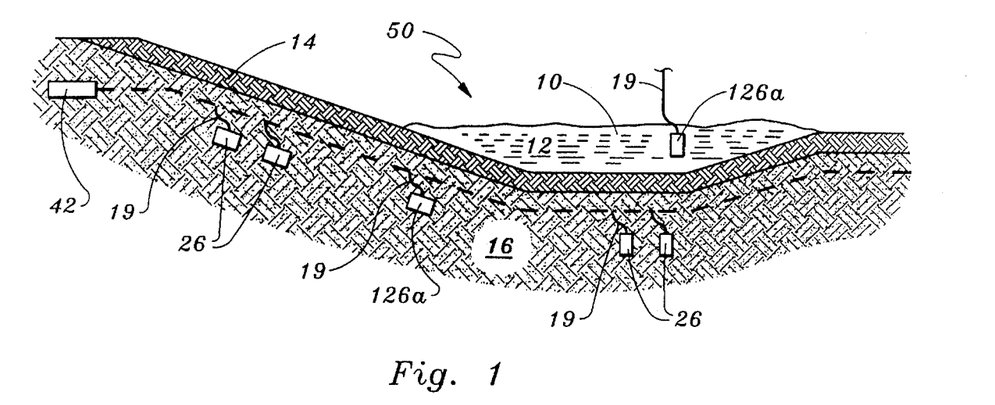
FIG. 1 is a side view depiction of the apparatus according to the present invention in its intended environment.

Referring to the drawings now wherein like reference numerals refer to like parts throughout the various drawing figures, reference numeral 50 is directed to the leak detector and locator according to the present invention. In essence, the detector 50 includes an array of probes 75 (FIG. 2) deployed below a liner 14 (FIG. 1). These probes 75 are operatively coupled to an analysis system 100, 110 shown in FIGS. 6 and 7. Collectively, this structure produces output in a three dimensional graph which represents either the existence of a leak (FIG. 4) or normal conditions (FIG. 3).

The geometry of the electric field is determined by first the positions of electrodes 26a (FIG. 2) used to inject the current and second, the configuration of the electrodes 26b used to measure the potential. The preferred embodiment uses a permanent electrode grid in an equally spaced rectangular arrangement within the sand or subgrade of the system. Four electrodes 26 in a row are preferred to take a measurement. An outer pair of electrodes 26a is used to inject the current and an inner pair of electrodes 26b measures the potential. The resistivity is computed at a virtual point 29 between the inner electrodes 26b. The virtual point 29 is called a measurement station. The preferred embodiment contemplates electrodes 26 spaced every one hundred feet in a ground liner system. The device manifests sufficient resolution to detect as little as fifty gallons of added liquid and then direct the search for the leak to an area within a fifty foot radius.

Referring now to FIG. 1, one embodiment of the detection system of the present invention is shown which is specifically adapted for use with a solution 12 reservoir. Although the embodiment shown in FIG. 1 is specifically directed to a lined liquid/sludge impoundment, it should be understood that the principles of the invention are applicable to a myriad of applications including, but not limited to: lined landfill cells, hazardous waste site cells, areas where migration of salinated water is suspected, lined water storage facilities, petroleum handling facilities, tank farms, or heap leach facilities.

As depicted in FIG. 1, storage channel 10 has been formed in the soil for the purpose of holding solution 12. Beneath storage channel 10 is geomembrane liner 14. In the event solution leaks from channel 10 through liner 14 and solution 12 permeates beyond geomembrane liner 14, a four-point probe 75 grid located within a leak detection layer 16 of FIG. 1, will register a leak when it occurs. Each four-point probe 75 operates as shown in FIG. 2.

Figure 5:
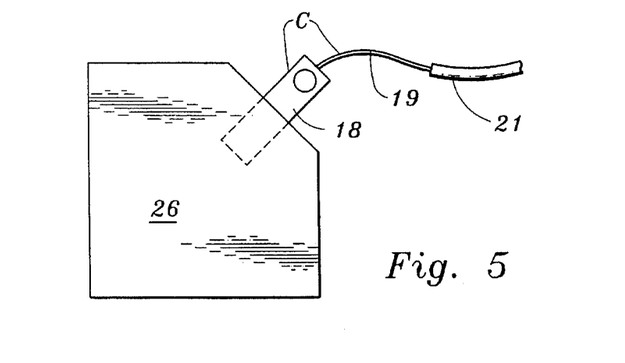
FIG. 5 is a map view of a typical electrode associated with the present invention.

In the preferred embodiment, the four-point probe 75 includes four stainless steel plates 26 also called electrodes 26 depicted in FIG. 5. Each plate 26 is a substantially rectangular construct having two opposing faces with surface areas significantly greater than the thickness of plate 26. Each plate 26 includes three 90° corners and one truncated corner such that a five edged construct is formed. Thus, one corner of a rectangular construct will have been mitered at 45°.

To better facilitate an effectual lead to plate 26, copper tab 18 is coupled to plate 26 at a midpoint of the mitered, truncated corner. Wire 19, formed of sixteen gage multistrand copper wire and covered with a high-density polyethylene jacket 21 rated for direct burial, then connects to plate 26 at copper tab 18. The tab 18 may be electrically coupled to the plate 26 by either embedment, soldering or both.

Figure 2:
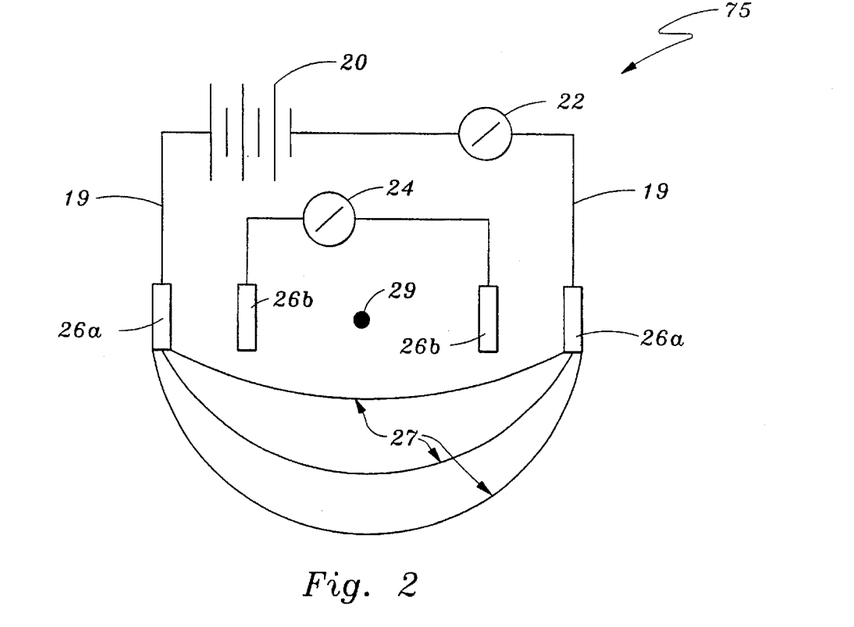
FIG. 2 is a schematic depiction of an electrode array in its operative mode and used as a measurement device.
Figure 3:
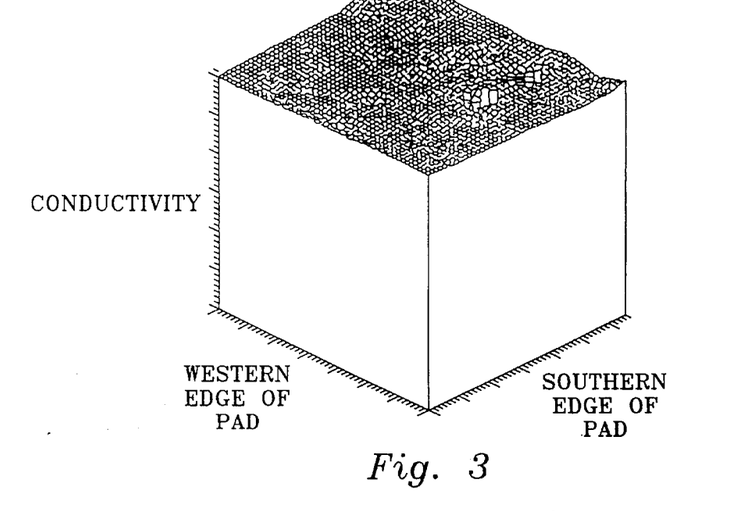
FIG. 3 is a three-dimensional graphic depiction of the area being surveiled according to the present invention.

As depicted in FIG. 2 an opposite end of wire 19 connects to either a power source 20 and current meter 22 or to a voltmeter 24. Each part of tab 18 and bare wire 19 is coated with electrical insulating varnish or equivalent waterproof coating so that no exposed copper exists uncovered.

In particular, as depicted in FIG. 2, when power supply 20 is energized, current flows through wire 19 to "outer" reference electrodes 26a–26a forming potential field 27. By means of current meter 22 connected in series with power supply 20 and reference electrodes 26a–26a, the applied current to the system may thus be readily determined. Further, by connecting volt meter 24 in parallel across "inner" detection electrodes 26b–26b, the voltage may be readily determined at measurement station 29 (virtual point).

Given the voltage and current, the following equations will then determine the resistivity:

$$Ra = K * V/I$$

where

V is the voltage measured by volt meter 24

I is the current measured by current meter 22 and constant $$K = 2 * \pi * (An/3)$$

where

AB denotes the distance between each current impressing electrode 26a.

Additionally, in terms of conductance (G), a more understandable quantity in these situations:

$G = 1/R_a$.

Although each data point may be determined manually, experience shows that it is more cost effective to have a computer system compile and distill the data into graphical reports. Such a system is depicted logically in FIG. 6 and graphically in FIG. 7. In particular, computer 40 causes analog measurements of voltage and current to be taken for measuring stations 29 in leak detection layer 16 by means of computer controllable switching devices contained in jack panel 42.

In essence, the computer switching moves from one four-point probe 75 to the next, where the next four-point probe 75 consists of three electrodes 26 from the first four-point probe 75 and one new electrode 26 in the row such that each measuring station 29 consists of a four-point probe 75 as depicted in FIG. 2. Analog signals, derived therefrom, are converted to digital signals by means of analog-to-digital converter (ADC) 44 such that computer 40 may store and compile that digital signal so that it may be compared to previously taken baseline data sets created during initialization of the electrodes with respect to the preexisting characteristics of the medium or displayed as raw data in terms of conductivity.

As mentioned infra "outer" electrodes 26a and "inner" electrodes 26b operate in concert to provide the leak surveillance. In actuality, the terms "inner" and "outer" are relative since the device 50 typically has a multiplicity of electrodes 26 well in excess of four which are oriented in a matrix 80 defining an R by C array where R is the number of rows and C is the number of columns. One electrode plate 26 is oriented at the intersection of each row and column. For example, and with reference to FIG. 7, a lined impoundment electric grid defines the leak detection layer 16. This matrix 80 or grid 80 is operatively coupled to the jack panel 42. Each of the "nodes" in the electric grid 80 is an ideal site for the disposition therewithin of one electrode plate 26. The surveillance and sampling involves sampling four electrodes 26 at a time such that the "outer" electrodes 26a impress thereon a current and the "inner" electrodes 26b monitor a voltage associated therewith.

Figure 7:
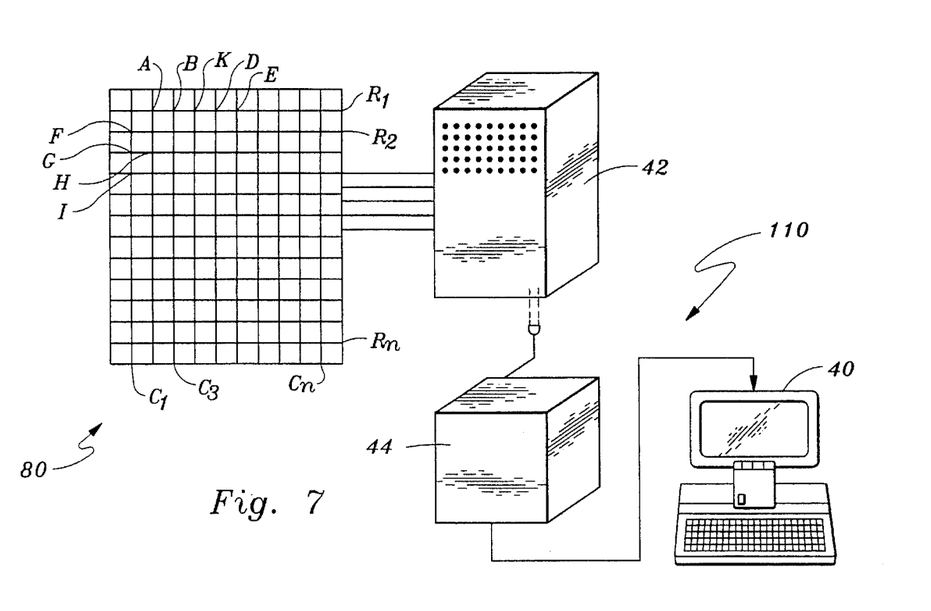
FIG. 7 is a further conceptual flow diagram associated with the present invention.

After one reading a subsequent reading again relying on four electrodes 26 is made, but one electrode 26 from the previous sample will have been dropped while another "new" electrode 26 will have been added. Therefore, as shown in FIG. 7, and by way of example, a first reading from grid 80 within layer 16 may be taken using plates 26 located at nodes A, B, K, D. A second reading may be taken by dropping electrode A and adding electrode E. Thus, the second reading would be comprised of electrodes B, K, D, E. In this example, the measurements are iteratively taken along one row R in the R by C array. Alternatively, the measurement could have been taken along a column such as column $C_2$. In this event, a first reading may utilize electrodes A, F, G, H. A successive reading may thereafter utilize electrodes F, G, H, I and so on.

In practice, it is intuitively proper to have all of the electrodes 26 substantially parallel one to the other although this is not necessary so long as proper initialization procedures are effected. Thus, mutual parallelism between adjacent or even all electrodes 26 is not necessary according to the instant invention, thereby making installation parameters less critical. The initialization proceeding would therefore become more important for standardization. Experimental data has shown that the field that emanates from any electrode conductive plate 26 is substantially spherical with minor edge effects adjacent the edges of the electrode 26. The initialization proceeding also initializes the electrodes with respect to the pre-existing characteristics of the medium to obtain a baseline measurement of potential difference between the electrodes representative of medium conductivity.

In an alternative embodiment (FIG. 1), a current source electrode 126a is located above the liner 14 within the solution 12. This current source electrode 126a replaces one of the electrodes 26a of the four-point probe 75. Thus, the grid of electrodes 26a, 26b is switched as a group of three electrodes rather then a group of four electrodes 26a, 26b. The three electrodes 26a, 26b consist of two voltage measuring electrodes 26b and one current sink electrode 26a.

Alternatively, the current sink electrode 26a may be replaced with a stationery current sink electrode 126a located above or below the liner 14. In this embodiment, the current field 27 is kept stationery and only the voltage measuring electrodes 26b are switched through the grid 16.

Figure 4:
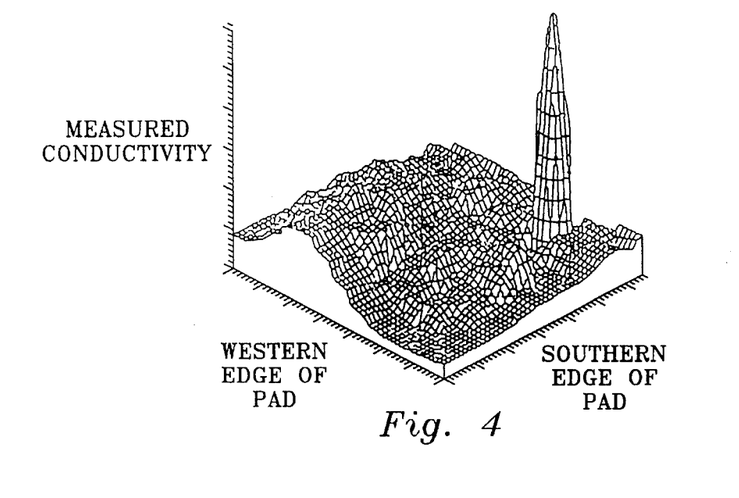
FIG. 4 is a view similar to FIG. 3 but showing the three-dimensional depiction after introduction of 200 gallons of solution in the lower right-hand portion of the FIG. 3 depiction.

To further assist a human user, with the aid of a graphical statistical interpretation program, the data may be displayed topographically as in FIG. 3 where a three dimensional plot consisting of the spatial coordinates of the measuring station on the grid 16 and the conductivity, G, measured at that station is shown. Further, should a leak be present, a topographical display will readily alert the viewer of such data to a problem as can be seen in FIG. 4, where the unusual peak depicts the location of a leak consisting of a material whose conductivity (G) is greater than the surrounding medium. Using the above described method of detection on a regular and daily basis allows additional analysis to be accomplished such as determination of random, periodic, seasonal and cyclic variations in the measured data. That is, compilation of soil conductivity data during a storm or during a particular season will allow a more accurate assessment of the measured data during a repeated rain or during a season in which soil conditions may change by comparing the most recent measurement to such archived data. The archived data can be established by archiving the conductivity measurements obtained at selected time intervals. By indexing each measurement with reference to prevailing conditions in existence at the time of the measurement, appropriate comparisons can be made between the most recent measurement and archived measurements indexed with similar prevailing conditions. The system can thus determine more accurately whether a leak has indeed occurred or whether instead, the soil conductivity (G) has changed due to the weather or seasonal changes.

Figure 8:
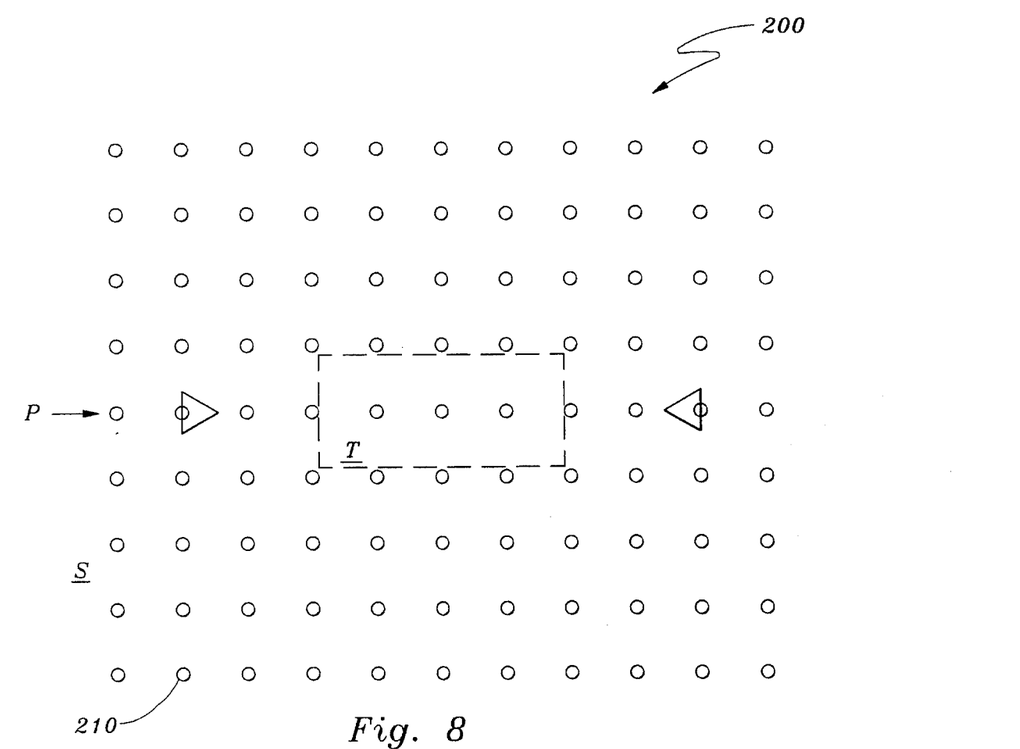
FIG. 8 is a top view of a region including a surface probe grid overlying a tank which is being monitored by the surface probe grid to detect leaks from the tank.
Figure 9:
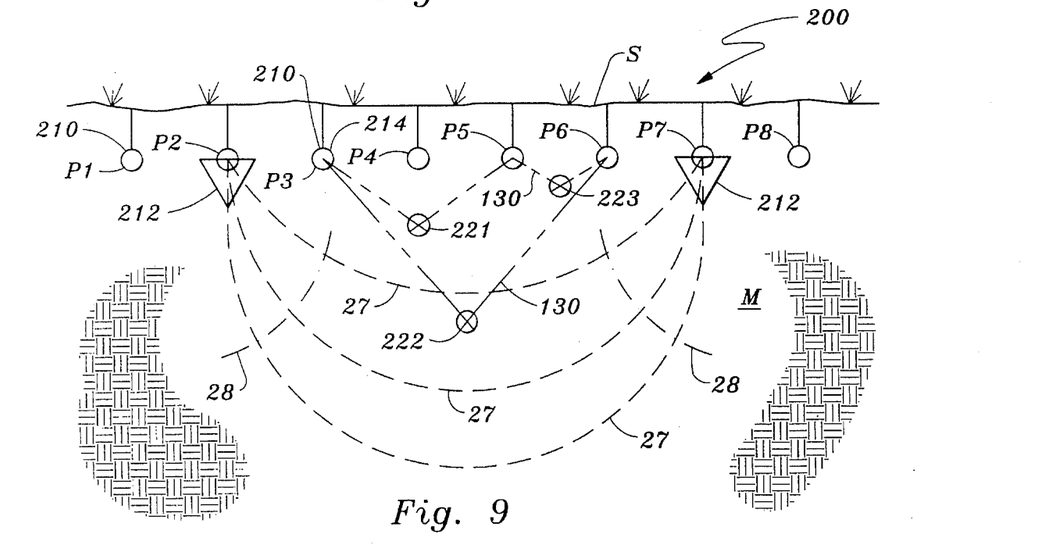
FIG. 9 is a side view of a region of sub-surface media which is being monitored by a plurality of surface probes, revealing conceptually the basis by which various different pseudo-point parameters are established.
Figure 10:
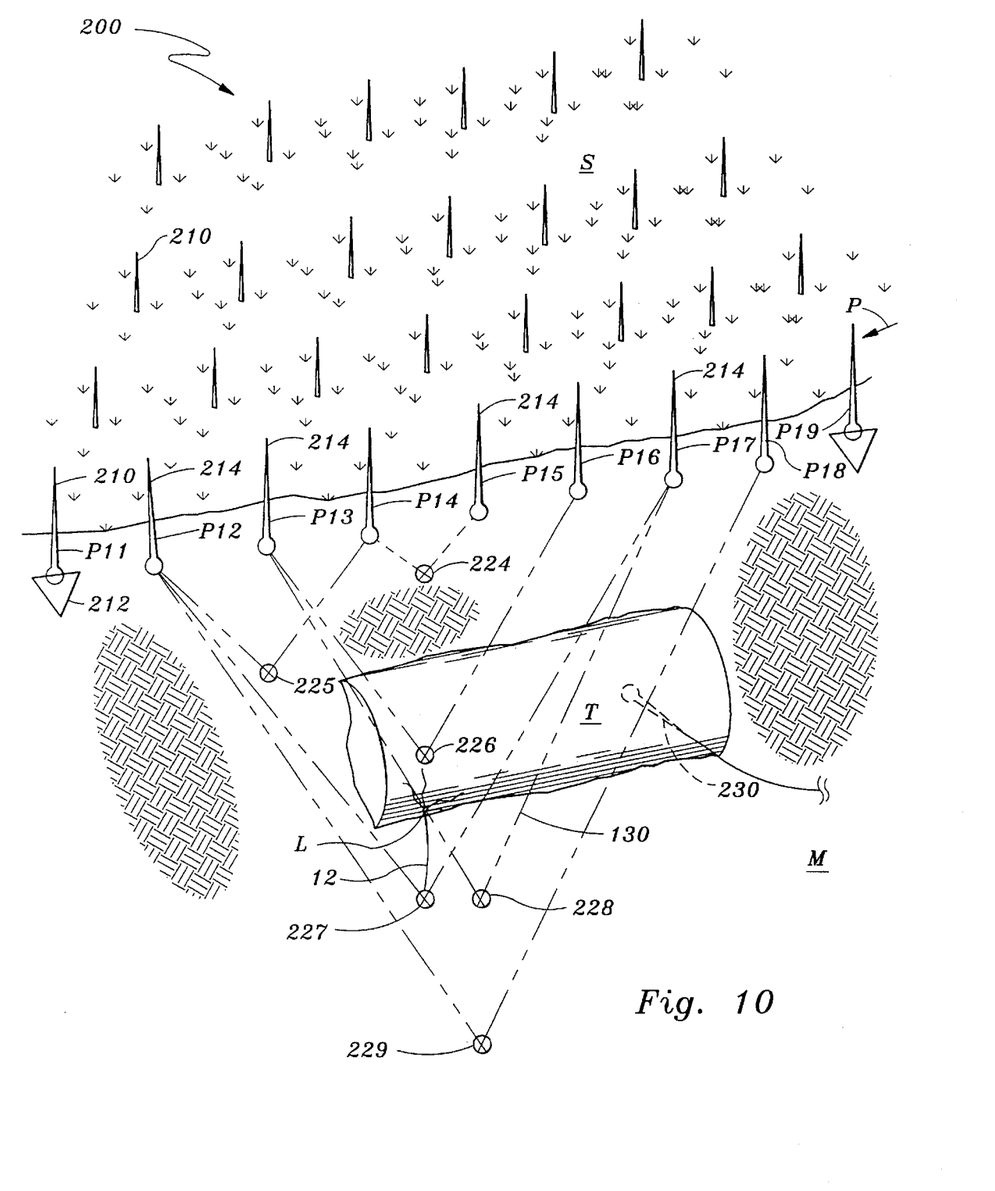
FIG. 10 is a perspective view of that which is show in FIG. 8 demonstrating an operation of the system of this invention according to a method which determines sub-surface conductivity at various pseudo-points in three dimensions, including depth.

With reference now to FIG. 8 through 10, details of a modified version of the leak detection system 50 are described in detail, particularly, the modified system is shown with a plurality of surface probes 210 adjacent a surface S which can overlie an impoundment such as a tank T. The modified system is utilized in a manner which allows for a conductivity of sub-surface media M to be determined for different points within the subsurface media M differing in location in three dimensions.

A surface probe grid 200 is provided with a plurality of surface probes 210 which extend at least partly beneath the surface S and into sub-surface media M. Preferably, the surface probes 210 are similar to the electrodes 26. The surface probes 210 can be arranged at a variety of different locations upon the surface S. However, the surface probes 210 are preferably oriented in a substantially square grid. Spacing between the surface probes 210 is dependent upon a size of the region to be monitored, a depth with which monitoring is desired, and a desired precision of the results to be obtained. In general, the greater the spacing of the surface probes 210, the greater the depth which can be monitored for conductivity. Precision is increased by locating the probes 210 closer together.

Figure 6:
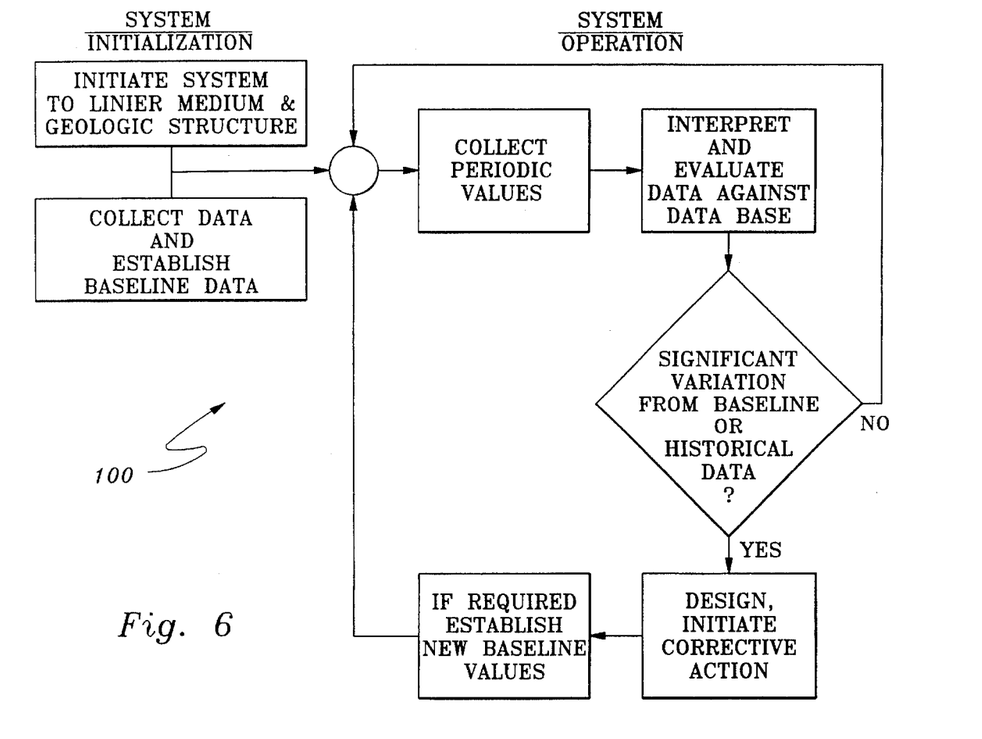
FIG. 6 is a flow chart associated with the utilization of the instant invention, showing its methodology.

As shown in FIG. 8, the surface probes 210 can be oriented to overlie a tank T to monitor the status of the tank T and detect whether or not the tank T is leaking, how much liquid is leaking from the tank T and the horizontal and vertical extent of a plume of leaking liquid. Each of the surface probes 210 is electrically coupled to an analysis system analogous to the analysis system 100, 110 (FIGS. 6 and 7). Preferably, this coupling is through insulated electric wires extending to the analysis system 100, 110.

The surface probes 210 are coupled to the analysis system 100, 110 with a coupling means such as insulated electric wire through the jack panel 42 (FIG. 7) such that the surface probes 210 can be selectively coupled to either the power source 20 (FIG. 2) which provides a voltage between two of the surface probes 210 or coupled to a volt meter 24, such that two of the surface probes 210 are coupled to the volt meter 24. The jack panel 42 thus provides a switching means to electrically couple the selected probes 210 to the power source 20 or the volt meter 24. The power source 20 has two output nodes which are coupled to the jack panel 42. These output nodes can be selectively coupled to any two individual surface probes 210. The volt meter has two sensing nodes which are coupled to the jack panel 42. These sensing nodes can be selectively coupled to any two individual surface probes 210.

With reference to FIG. 9, a side view of the sub-surface media M and a surface S being monitored for sub-surface soil conductivity is shown. FIG. 9 reveals a vertical plane which includes a plurality of surface probes 210 therein extending slightly below the surface S. Each surface probe 210 is at any given time either inactive, such as probes P1, P4 and P8; an active probe 212 coupled to the power source 20, such as probes P2 and P7; or a monitoring probe 214, such as probes P3, P5 and P6 which are coupled to the volt meter 24. While any individual surface probe 210 may at one time be inactive, it can later become an active probe 212 by being coupled to the power source 220 and then still later become a monitoring probe 214 by being coupled to the volt meter 24. However, preferably each surface probe 210 never has dual status as both an active probe 212 and a monitoring probe 214.

The active probes 212 in FIG. 9 are represented with equilateral triangles connected thereto to indicate that current is being impressed into the sub-surface media M between the active probes 212, probes P2 and P7. This current is represented by flux lines 27 extending between the probes P2, P7. A potential difference between the probes P2, P7 would essentially be similar to a potential difference across the power source 20 (FIG. 2).

A plurality of equal potential lines 28 are oriented substantially perpendicular to the flux lines 27 and oriented between the probes P2, P7. These equal potential lines 28 show lines where a common electromotive potential exists. No current would travel in a direction parallel to such lines. Thus, two surface probes 210 oriented along a common equal potential line 28 would have no electromotive potential therebetween and, if configured as monitoring probes 214 coupled to the volt meter 24, would result in the volt meter 24 indicating no voltage between the two monitoring probes 214. If two monitoring probes 214 are selected which are not on the same equal potential lines 28, a voltage would be indicated by the volt meter 24. This voltage represented by the volt meter 24 would correspond with a voltage difference between the equal potential lines 28 passing through the two monitoring probes 214.

In sub-surface media M having uniform conductivity, generally the further apart the surface probes 210 are, the greater a voltage between those two surface probes 210 when the active probes 212 are also surface probes 210 and the surface S is substantially planar. However, when the sub-surface media M is non-uniform in conductivity voltage differences between monitoring probes 214 would not necessarily be correlated to a distance between the monitoring probes 214. This divergence in a voltage detected by the volt meter 24 between two monitoring probes 214 is thus indicative of anomalous conductivity exhibited by the sub-surface media M in a region adjacent to the monitoring probes 214.

To adequately monitor the entire region of sub-surface media M, the jack panel 42 can be used as a switching means to switch the volt meter 24 to be coupled to a variety of different surface probes 210. A variety of different surface probes 210 can thus act as monitoring probes 214 and monitor conductivity at various regions within the subsurface media M. It has been determined that one effective way to represent the conductivity of sub-surface media M is to identify a plurality of pseudo-points. Each pseudo-point has a variety of parameters including a location for that pseudo-point and a conductivity value representative of a conductivity of the sub-surface media at that pseudo-point location.

The values for the pseudo-point parameters can be calculated for a variety of different pseudo-points. This information can then be outputted so that a user can make a judgment as to whether or not a leak exists or what the condition of sub-surface media conductivity is based on the conductivity values for the various pseudo-points. These pseudo-point conductivity values can be updated periodically and compared with previous conductivity values for pseudo-points at the same locations to identify trends which could be indicative of changes in sub-surface media M soil moisture, indicative of a leak.

A location parameter of each pseudo-point includes both a surface position identifying a point on the surface S directly above the pseudo-point and a depth of the pseudo-point beneath the surface S. The surface position S of the pseudo-point is preferably a location exactly halfway between the two monitoring probes 214 utilized in detecting the conductivity for that pseudo-point. By way of example, and with reference to FIG. 9, pseudo-point 221 has a location parameter including a surface position at probe P4. This is because probe P4 is approximately halfway between the two probes P3 and P5 used as monitoring probes 214 when the pseudo-point 221 is established.

It has been determined that a depth for each pseudo-point can also be calculated and provide a user with an indication of soil moisture and conductivity changes at various different depths. A depth of the pseudo-point is generally a function of a distance between the monitoring probes 214 utilized to measure a conductivity of the sub-surface media M for that pseudo-point. A depth of the pseudo-point is directly proportional to a distance between the monitoring probes 214. Thus, when monitoring probes 214 are widely spaced apart, pseudo-points having a great depth are monitored. When monitoring probes 214 are located more closely together, pseudo-points having a shallower depth are monitored.

One method for determining more precisely the correlation between monitoring probe 214 spacing and pseudo-point depth involves a calibration process. Initially, pairs of monitoring probes 214 are utilized which have varying spacing but which are all oriented in a common vertical plane and are spaced from a point on the surface S directly above the pseudo-point, an amount equal to a spacing of the corresponding monitoring probe 214 of that pair. Thus, each pseudo-point for each pair of monitoring probes 214 exhibits a common surface location parameter.

Once a variety of different monitoring probes 214 have been utilized to establish a plurality of pseudo-points beneath this surface location, a liquid having a conductivity distinct from the sub-surface media M is injected at a known depth below the surface location. This injection can occur by drilling a hole into the media M to the designated depth and then placing a tube open on the bottom within the hole. Liquid can then be injected out the bottom of the tube. Conductivity values for the pseudo-points are then recalculated. Those pseudo-points whose conductivities failed to change significantly upon introduction of the liquid at the known depth are considered to have a depth above or below the known depth of liquid injection. Those pseudo-points which exhibit a noticeable change in their conductivity parameters, are considered to be near the depth at which the liquid was injected. By repeating this liquid injection at known depths and repeatedly monitoring changes in conductivity, the system 650 can be calibrated so that a depth parameter of the pseudo-points can be reliably determined.

As shown in FIG. 9, when adjacent probes P5 and P6 are utilized as monitoring probes 214, a pseudo-point 223 is established approximately halfway between the two monitoring probes 214 and having a relatively shallow depth due to the relative proximity of surface probes P5, P6. When surface probes P3 and P5 are utilized as monitoring probes 214, pseudo-point 221 is established having a location parameter substantially halfway between the surface probes P3 and P5 and having a somewhat substantial depth due to the somewhat substantial distance between the surface probes P3, P5. When surface probes P3 and P6 are utilized as monitoring probes 214, pseudo-point 222 is established having a location parameter substantially halfway between the two monitoring probes 214 and having a more substantial depth due to the relative distance of surface probes P3 and P6. By utilizing the calibration process discussed above, or other calibration methods known in the art, more precise formulas for the exact location parameters of each pseudo-point can be calculated.

A conductivity parameter of each pseudo-point can be calculated in the following manner. With two active probes 212 impressing current into the sub-surface media M, the volt meter 24 is coupled to two monitoring probes 214. In the manner discussed above, a location parameter of the pseudo-point is provided corresponding to the location of the monitoring probes 214. The volt meter 24 then measures a voltage between the monitoring probes 214. A current measured by current meter 22 (FIG. 2) can then be divided by a voltage measured by the volt meter 24 to determine the conductivity parameter for that pseudo-point. Thus, all of the parameters for the pseudo-point, including location parameters and conductivity parameters, can be accordingly calculated.

Preferably, another parameter for the pseudo-point is the time at which the conductivity parameter is determined. In this manner, comparisons can be made for specific pseudo-points which detect changes in conductivity over time for that pseudo-point. Such information can be indicative of changes in the sub-surface conductivity of the media M, such as that due to a leak from an enclosure such as a tank T.

In use and operation, and with particular reference to FIG. 10, the method and system for sub-surface leak detection in three dimensions is further described. As discussed above, one use for the leak detection system 50 is in detection of leaks L from impoundments such as liquid storage tanks T. Such tanks T can be oriented upon the surface and the subsurface media M can be monitored for migration of liquid out of the tank T and into the underlying sub-surface media M. Also, the tank T can be buried within the sub-surface media M and the surrounding sub-surface media M can be monitored for conductivity changes indicative of leaks L from the tank T.

Initially, the surface probe grid 200 of surface probes 210 is arranged in an array adjacent the surface S overlying the tank T to be monitored. Preferably, the surface probes 210 extend at least partially beneath the surface S such that electrically conductive surfaces of the surface probes 210 are in intimate contact with the sub-surface media M. Preferably, the leak detection system is primarily utilized in a plurality of different vertical planes P which include a plurality of the surface probes 210 therein. A variety of different pseudo-points within this vertical plane P can thus be established.

The values for these pseudo-points can be verified by utilizing appropriate active probes 212 and monitoring probes 214 in a separate plane which intersects the plane P at one of the pseudo-points, the monitoring probes 214 spaced such that an identical pseudo-point can be monitored. Identification of similar conductivity for that pseudo-point acts as a check that the system is working properly. If greatly diverging conductivities are detected, this can be indicative of anomalous conductivities exhibited by the sub-surface media M which can be of assistance in further calibrating the system to effectively monitor the sub-surface media M.

Preferably, the surface probes 210 which are utilized as active probes 212 are oriented within the same probe plane P as the monitoring probes 214. Preferably, the active probes 212 are the two most greatly spaced surface probes 210 within that probe plane P. Thus, all of the monitoring probes 214 are between the two active probes 212. As shown in FIG. 10, surface probes P11 and P19 are utilized as active probes 212. As illustrated in FIG. 10, the tank T includes a leak L at a bottom portion of the tank T. The system can then be utilized as discussed above to establish parameters for a variety of different pseudo-points throughout the sub-surface media M region to be monitored.

When the surface probes P14 and P15 are utilized, a pseudo-point 224 is established. When the surface probes P12 and P14 are utilized a pseudo-point 225 is established. When the surface probes P13 and P16 are utilized, a pseudo-point 226 is established. When the surface probes P12 and P17 are utilized, a pseudo-point 227 is established. When the surface probes P13 and P17 are utilized, a pseudo-point 228 is established. When the surface probes P12 and P18 are utilized, a pseudo-point 229 is established. Similarly, a multiplicity of additional pseudo-points can be established.

As shown in FIG. 10, pseudo-points 224 through 226 are too low or too far spaced laterally from the leak L to exhibit sufficient changes in their conductivity parameter to indicate that a leak L has occurred. The pseudo-points 228 and 229 are too deep to detect any portion of the leaking liquid solution 12 plume. However, the pseudo-point 227 is adequately positioned to detect increased conductivity due to the presence of the liquid leak L plume. Thus, the pseudo-point 227 would have a conductivity parameter which would increase if the liquid leaking from the tank T has a higher conductivity than the surrounding sub-surface media M. As is readily apparent, by utilizing different monitoring probes 214, both within the vertical plane P and in other vertical planes P which include the tank T and the leak L, further information as to the extent of the leak L can be determined.

The equidistance lines 130 extending between the pseudo-points (221 through 229) and the monitoring probes 214 identify the surface probes 210 to which the pseudo-points (221 through 229) correspond. These equidistance lines 130 are shown to be generally of similar distance between each pseudo-point (221 through 229) and the two monitoring probes 214 which are utilized to establish the conductivity parameter for that pseudo-point. As discussed above, a location parameter for each pseudo-point can be calculated from the positions of the monitoring probes 214 utilized to provide the conductivity parameters for those pseudo-points and also by utilizing the information obtained from calibration of the surface probe grid 200.

As a modification to the system embodiment disclosed in FIGS. 8 through 10, the active probes 212 can be replaced with one internal probe 230 oriented within the tank T and a second active probe 212 oriented somewhere outside the tank T, such as one of the surface probes 210. Such location of one of the active probes 212 within the tank is particularly effective where walls of the tank T are non-conductive. Thus, if a leak L occurs in the tank T, a current pathway is established through the tank T which can be detected by utilizing the internal probe 230 and a plurality of monitoring probes 214 as discussed in detail above.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An apparatus for detecting and locating a leak from an impoundment, the impoundment confining a substance to be impounded above a soil substrate, the apparatus, comprising, in combination:

said soil substrate underlying and conformed to mirror the impoundment;

a plurality of sensing means;

means for establishing parameters of a plurality of pseudo-points within said soil substrate;

said parameters including a location parameter and a conductivity parameter for each said plurality of pseudo-points;

each said location parameter correlating a location of at least one said pseudo-point to each individual said sensing means and other proximate said sensing means; and each said conductivity parameter correlating a conductivity of at least one said pseudo-point to each individual said sensing means and other proximate said sensing means:

means for processing and storing said location parameter and said conductivity parameter for each said plurality of pseudo-points;

a current supply directed to a region proximate to said plurality of sensing means such that a potential difference is established between at least one pair of said plurality of sensing means when said current supply is energized;

each of said sensing means oriented in a fixed location embedded within the soil substrate;

the impoundment provided with a substance, which when admitted to the soil substrate alters the potential difference between at least one said pair of said plurality of sensing means; and monitoring means operatively coupled to said plurality of sensing means for detecting the potential difference between at least one said pair of said plurality of sensing means; and means for determining a resultant conductivity parameter for at least one said pair of said plurality of sensing means in which the potential difference is detected; and means for comparing said resultant conductivity parameter of at least one said pair of said plurality of sensing means with said conductivity parameter of at least one said pseudo-point established for at least the one said pair of said plurality of sensing means for detecting and locating the admittance of the substance from the impoundment into the soil substrate.

2. The apparatus of claim 1 wherein said sensing means are arranged in an array consisting of rows and columns.

3. The apparatus of claim 2 wherein said sensing means are ganged in clusters of four.

4. The apparatus of claim 3 wherein said sensing means consist of solid plates.

5. The apparatus of claim 4 wherein said solid plates have one mitered corner.

6. The apparatus of claim 5 wherein said mitered corner is affixed to a copper lead which is connected to heavy gage insulated wire.

7. The apparatus of claim 6 wherein said copper lead and an exposed portion of said wire is coated with a waterproof substance.

8. The apparatus of claim 1 wherein said monitoring means consists of a voltage measuring means and a current measuring means.

9. The apparatus of claim 8 wherein said current measuring means is connected in series between said current supply means and two sensing means.

10. The apparatus of claim 9 wherein said voltage measuring means is connected in parallel across two other sensing means situated between said two sensing means which are connected to said current measuring means and said current supply means.

11. The apparatus of claim 10 wherein said voltage measuring means and said current measuring means include switching means interposed between each said sensing means and said voltage measuring means and said current measuring means, said switching means iteratively connecting said voltage measuring means and said current measuring means to different said sensing means, such that each sensing means is selectively coupled to either said voltage measuring means or said current measuring means and selectively decoupled and recoupled to said voltage measuring means and said current measuring means in a different orientation.

12. The apparatus of claim 11 wherein said switching means are engaged by a computer means.

13. The apparatus of claim 12 wherein said voltage measuring means and said current measuring means are connected to an analog to digital converter (ADC).

14. The apparatus of claim 13 wherein said ADC is connected to said computer means.

15. A system for monitoring the soil beneath an impoundment of fluid to be confined for the presence of a leak in the impoundment, comprising, in combination:

a plurality of electrodes, means for establishing parameters of a plurality of pseudo-points within the soil adjacent the impoundment wherein at least one said pseudo-point is associated with each individual said electrode and other proximate said electrodes, said parameters including a pseudo-point potential profile parameter for each said plurality of pseudo-points;

each said pseudo-point potential profile parameter correlates a potential difference between a pair of said plurality of electrodes in which said pseudo-point is associated with, means for processing and storing said parameters for each said plurality of pseudo-points, said plurality of electrodes each having directional sensitivity and all mutually oriented with respect to one another such that when a current is impressed on any one pair of said plurality of electrodes by a source of current, a potential profile is impressed upon another pair of said plurality of electrodes, said electrodes permanently embedded beneath the impoundment such that a leak from the impoundment changes the potential profile between said electrodes, and monitoring means coupled to said electrodes to monitor and calculate values of the potential profile between any pair of said plurality of electrodes, and means for comparing said potential profile between any pair of said plurality of electrodes with said pseudo-point potential profile parameter associated with said pair of said plurality of electrodes for detecting a leak in the impoundment.

16. The system of claim 15 including iterating means to move said source of current from one pair of electrodes to another and to monitor the potential from one pair of electrodes to another, such that each electrode is selectively switched from being coupled to said source of the current to being coupled to said potential monitoring means.

17. The system of claim 15 including iterating means to move voltage sensing from one pair of electrodes to another pair of said plurality of electrodes, and wherein said monitoring means includes means for calculating a difference between more recent values and less recent values, the difference indicating a change in resistivity of the soil indicative of a leak in the impoundment.

18. A system for monitoring changes in the salinity of portions of an underground aquifer comprising in combination:

a plurality of electrodes;

means for establishing parameters of a plurality of pseudo-points within underground soil;

said parameters including a location parameter and a resistivity parameter for each said plurality of pseudo-points;

each said location parameter correlating a location of at least one said pseudo-point to each individual electrode and other proximate electrodes, each said resistivity parameter correlating a resistivity of at least one said pseudo-point to each individual electrode and other proximate electrodes, said plurality of electrodes oriented in an array and having directional sensitivity such that when an electric current from a current source is impressed on two electrodes of the array a potential difference is imposed between two other electrodes in the array, said electrodes positioned along a region where salinated water migration is suspected;

wherein a computation means is operatively coupled to said electrodes and calculates the potential difference between said electrodes, said computation means including a means to determine a resultant resistivity of the underground soil between said electrodes;

wherein said computation means includes a means for calculating a difference between the resultant resistivity between said electrodes and the resistivity of at least one said pseudo-point associated with said electrode; and wherein a switching means is interposed between said current source and said electrodes, said switching means also interposed between said computation means and said electrodes, such that said electrodes are selectively connected and disconnected iteratively to either said current source or said computation means;

whereby when salinated water penetrates soil surrounding said electrodes, the resistivity of at least one said pseudo-point within the soil is decreased due to the different electrolytic properties of salinated water indicating that salinated water migration is occurring.

19. The system of claim 18 wherein the resistivity (R) of the soil is determined from the potential difference (V) imposed between said electrodes and the current (I) impressed by other said electrodes through the equation:

$$R=K*V/I$$

where $K$=constant represented by $2*\pi*(AB/3)$ and AB is the distance between outer, current source electrodes, or alternatively a first potential difference sensing electrode, from a current sink;

whereby K can be calculated in advance of R measurements and R can be determined directly from V when a current input (I) is sent through said current source electrode and said current sink.

20. A method for detecting changes in conductivity of sub-surface media, indicative of an event such as a leak, including the steps of:

orienting a plurality of probes in a grid with each probe having at least a portion thereof beneath a surface overlying a sub-surface region to be monitored, each probe formed to include conductive material exposed on a surface of the probe, the conductive material in contact with media beneath said surface;

coupling each probe electrically to a switching means, said switching means including means to selectively connect at least two of the probes to a volt meter;

impressing a current into the sub-surface media;

operating the switching means to couple a first set of at least two probes to the volt meter such that the at least two probes become voltage monitoring probes;

measuring a voltage between the at least two probes;

calculating a conductivity of sub-surface media between the first set of probes by dividing the current by the voltage;

re-operating the switching means to couple a second set of at least two probes to the volt meter;

determining a conductivity of sub-surface media between the second set of probes by repeating said measuring step and said calculating step for the second set of probes;

continuing to re-operate said switching means and repeat said determining step until the region identified for event monitoring has been covered;

establishing parameters for a plurality of pseudo-points, each pseudo-point including a location parameter which identifies a location of the pseudo-point in three-dimensional space and a conductivity parameter representative of an electric conductivity of sub-surface media adjacent the pseudo-point, said location parameter including a surface position representative of a point on the surface directly above the pseudo-point and a depth, the surface position of said location parameter equal to a midpoint between the two voltage monitoring probes utilized in said determining step to determine a value of the conductivity parameter for the pseudo-point, the depth of said location parameter being a function of a distance between the two monitoring probes utilized in said determining step to determine the value of the conductivity parameter for the pseudo-point.

21. A method for detecting changes in conductivity of sub-surface media, indicative of an event such as a leak, including the steps of:

orienting a plurality of probes in a grid with each probe having at least a portion thereof beneath a surface overlying a sub-surface region to be monitored, each probe formed to include conductive material exposed on a surface of the probe, the conductive material in contact with media beneath said surface;

coupling each probe electrically to a switching means, said switching means including means to selectively connect two of the probes to a volt meter;

impressing a current into the sub-surface media;

operating the switching means to couple a first set of two probes to the volt meter such that the two probes become voltage monitoring probes;

measuring a voltage between the two probes;

calculating a conductivity of sub-surface media between the first set of probes by dividing the current by the voltage;

re-operating the switching means to couple a second set of two probes to the volt meter;

determining a conductivity of sub-surface media between the second set of probes by repeating said measuring step and said calculating step for the second set of probes;

continuing to re-operate said switching means and repeat said determining step until the region identified for event monitoring has been covered;

establishing parameters for a plurality of pseudo-points, each pseudo-point including a location parameter which identifies a location of the pseudo-point in three-dimensional space and a conductivity parameter representative of an electric conductivity of sub-surface media adjacent the pseudo-point, said location parameter including a surface position representative of a point on the surface directly above the pseudo-point and a depth, the surface position of said location parameter equal to a midpoint between the two voltage monitoring probes utilized in said determining step to determine a value of the conductivity parameter for the pseudo-point, the depth of said location parameter being a function of a distance between the two monitoring probes utilized in said determining step to determine the value of the conductivity parameter for the pseudo-point.

22. The method of claim 21 wherein said impressing a current step includes the steps of:

providing a power supply between a set of two probes such that they become active probes, positioning the two active probes with at least a portion thereof beneath the surface, interposing a switching means between the two active probes and the power supply, providing additional sets of active probes having at least a portion thereof beneath the surface and coupled to the switching means, and operating the switching means to electrically connect the power supply to two probes from which electric current discharge into the sub-surface media is desired.

23. The method of claim 22 including the further steps of:

aligning the active probes and a first two monitoring probes in a common vertical plane with the active probes spaced further from each other than the probes of said determining step and with both of the monitoring probes between the active probes, impressing a current into the sub-surface media through the active probes, determining a conductivity of a pseudo-point corresponding to the first two monitoring probes, operating the switching means to couple the volt meter to a new set of two probes, said new set of two probes oriented within the common vertical plane with both of the new probes between the first two monitoring probes, and providing a pseudo-point between the two new probes with a location parameter including a depth which is less than a location parameter depth of the first two monitoring probes, whereby conductivity at various surface locations and depths within a sub-surface region can be determined.

24. The method of claim 23 including the further step of continuing to determine the conductivity parameter for pseudo-points throughout a region of interest at different times, comparing conductivity parameters for each pseudo-point as a function of time, and identifying changes in conductivity parameters of the pseudo-points within a region of interest, correlating to an event such as a leak.

25. The method of claim 24 including the further steps of:

orienting the monitoring probes and the active probes imbedded within sub-surface media adjacent a surface overlying an underground containment vessel, establishing values for location and conductivity parameters of pseudo-points surrounding the containment vessel, and updating conductivity parameters for the pseudo-points at successive time intervals.

26. A system for monitoring conductivity of subsurface media, comprising in combination:

a plurality of probes, each probe including an electrically conductive material exposed on a surface of said probe and means to couple said probe electrically to other components of said system, said probes including means to allow burial thereof at least partially beneath a surface overlying a region of sub-surface media to be monitored, a power source having two output nodes and means to impose a voltage between said output nodes, a volt meter having two sensing nodes, means to measure a voltage between said sensing nodes, and means to communicate a voltage measured by said measuring means to an output device, and a switching means including:
  means to selectively electrically couple each of said two output nodes to a different one of a first pair of said probes, such that said first pair of said probes become active probes delivering current into a portion of the sub-surface media between said active probes,
  means to selectively electrically couple each of said two sensing nodes to a different one of a second pair of said probes, such that said second pair of said probes become monitoring probes monitoring a voltage between said monitoring probes caused by said current between said active probes;

means to establish a location parameter and a conductivity parameter for a plurality of pseudo-points, said location parameter representing a position of said pseudo-point in three dimensional space and said conductivity parameter representing a conductivity of said sub-surface media adjacent the location of said pseudo-point, said location parameter including a surface location directly above said pseudo-point and a depth representing a distance from said pseudo-point to said surface location, said surface location of said location parameter halfway between locations of said monitoring probes and said depth portion of said location parameter being a function of a distance between said monitoring probes, said conductivity parameter calculated by dividing the current generated by said power source by the voltage detected by said volt meter, whereby a conductivity of said subsurface media at a plurality of pseudo-points within the sub-surface media of the region to be monitored can be determined.

27. The system of claim 26 further including a means to calculate a conductivity of the sub-surface media at a plurality of pseudo-points approximately halfway between said monitoring probes by dividing the current delivered by said active probes with a voltage detected by said monitoring probes.

28. A system for monitoring conductivity of subsurface media, comprising in combination:

a plurality of probes, each probe including an electrically conductive material exposed on a surface of said probe and means to couple said probe electrically to other components of said system, said probes including means to allow burial thereof at least partially beneath a surface overlying a region of sub-surface media to be monitored, a power source having two output nodes and means to impose a voltage between said output nodes, a volt meter having two sensing nodes, means to measure a voltage between said sensing nodes, and means to communicate a voltage measured by said measuring means to an output device, and a switching means including:

means to selectively electrically couple each of said two output nodes to a different one of a first pair of said probes, such that said first pair of said probes become active probes delivering current into a portion of the sub-surface media between said active probes;

means to selectively electrically couple each of said two sensing nodes to a different one of a second pair of said probes, such that said second pair of said probes become monitoring probes monitoring a voltage between said monitoring probes caused by said current between said active probes;

means to calculate a conductivity of the sub-surface media at a plurality of pseudo-points approximately halfway between said monitoring probes by dividing the current delivered by said active probes with a voltage detected by said monitoring probes;

means to establish a location parameter and a conductivity parameter for a plurality of said pseudo-points, said location parameter representing a position of said pseudo-point in three dimensional space and said conductivity parameter representing a conductivity of said sub-surface media adjacent the location of said pseudo-point, said location parameter including a surface location directly above said pseudo-point and a depth representing a distance from said pseudo-point to said surface location, said surface location of said location parameter halfway between locations of said monitoring probes and said depth portion of said location parameter being a function of a distance between said monitoring probes, said conductivity parameter calculated by dividing the current generated by said power source by the voltage detected by said volt meter, whereby a conductivity of said subsurface media at a plurality of pseudo-points within the sub-surface media of the region to be monitored can be determined.

29. The system of claim 28 wherein said active probes and said monitoring probes for each pseudo-point are oriented in a common vertical plane with said monitoring probes located closer to each other than said active probes and both of said monitoring probes between said active probes.

30. A system for monitoring the soil beneath an impoundment of fluid to be confined for the presence of a leak in the impoundment, comprising, in combination:

a plurality of electrodes, each having directional sensitivity and all mutually oriented with respect to one another such that when a current is impressed on any one pair of electrodes by a source of current, a potential difference is impressed upon another pair, said electrodes permanently embedded beneath the impoundment such that a leak from the impoundment changes the potential difference between said electrodes, and monitoring means coupled to said electrodes to monitor and calculate values of the potential difference, iterating means to move said source of current from one pair of electrodes to another and to monitor the potential difference from one pair of electrodes to another, such that each electrode is selectively switched from being coupled to said source of the current to being coupled to said potential monitoring means, iterating means to move said monitoring means from one pair of electrodes to another pair of said plurality of electrodes, said monitoring means includes means for calculating a difference between more recent values and less recent values of potential difference, the difference indicating a change in resistivity of the soil indicative of a leak in the impoundment, wherein the resistivity (R) of the soil is determined from the potential difference (V) imposed between said electrodes and the current (I) impressed by other said electrodes through the equation:

$$R = K * V/I$$

where $$K = \text{constant represented by } 2*\pi*(AB/3)$$

and AB is the distance between any one said pair of electrodes in which current is impressed, and whereby K can be calculated in advance of (R) measurements and (R) can be determined directly from (V) when current input (I) is impressed on any one said pair of electrodes.

31. A system for monitoring the soil beneath an impoundment of fluid to be confined for the presence of a leak in the impoundment, comprising, in combination:

a plurality of electrodes, each having directional sensitivity and all mutually oriented with respect to one another such that when a current (I) is impressed on any one pair of electrodes by a source of current, a potential difference (V) is impressed upon another pair, said electrodes permanently embedded beneath the impoundment such that a leak from the impoundment changes the potential difference (V) between said electrodes, and monitoring means coupled to said electrodes to monitor and calculate values of the potential difference (V);

wherein a resistivity (R) of the soil is determined from the potential difference (V) imposed between said electrodes and the current (I) impressed on any one said pair of electrodes through the equation:

$$R = K*V/I$$

where $$K = \text{constant represented by } 2*\pi*(AB/3)$$

and AB is the distance between any one said pair of electrodes in which current is impressed; and whereby K is calculated in advance of (R) measurements and (R) is determined directly from (V) when the current (I) is impressed on any one said pair of electrodes.

32. A system for monitoring conductivity of subsurface media, comprising in combination:

a plurality of sensing means;

means for establishing parameters of a plurality of pseudo-points within said subsurface media wherein at least one said pseudo-point is associated with each individual said sensing means and other proximate said sensing means;

each said pseudo-point including a conductivity parameter representative of an electric conductivity of the sub-surface media adjacent said pseudo-point;

means for processing and storing said conductivity parameter for each said plurality of pseudo-points;

monitoring means operatively coupled to said plurality of sensing means for identifying any change in the conductivity parameter established for each said pseudo-point correlating to an event such as a leak from an impoundment of fluid proximate the subsurface media.

33. The system of claim 32 wherein each said pseudo-point further includes a location parameter which identifies a location of each said pseudo-point in three dimensional space.

34. The system of claim 33 wherein each said location parameter is processed and stored by said processing and storing means whereby each said conductivity parameter of each said pseudo-point is identified in three dimensional space.

35. The system of claim 34 further including means for updating said conductivity parameters for said pseudo-points at successive time intervals.

* * * * *